United States Patent [19]

Hessel

[11] 4,375,813
[45] Mar. 8, 1983

[54] MEDICAL FLUID FLOW RATE CONTROLLING DEVICE

[75] Inventor: Stephen R. Hessel, Monroe, Conn.

[73] Assignee: Delmed, Inc., Canton, Mass.

[21] Appl. No.: 233,095

[22] Filed: Feb. 10, 1981

[51] Int. Cl.³ ............................................. A61M 5/14
[52] U.S. Cl. ................................. 128/214 C; 128/227
[58] Field of Search .......... 128/214 R, 214 C, 214 G, 128/214.2, 227

[56] References Cited

U.S. PATENT DOCUMENTS

| | | | |
|---|---|---|---|
| 1,205,410 | 11/1916 | Tenney | |
| 1,338,782 | 5/1920 | Lindahl | |
| 1,427,455 | 8/1922 | Gates | |
| 1,844,342 | 2/1932 | Berman | |
| 2,090,273 | 8/1937 | Wagner | 137/68 |
| 2,254,833 | 9/1941 | Ashkenaz | 128/213 |
| 2,479,786 | 8/1949 | Stevens | 73/216 |
| 2,865,534 | 12/1958 | Barnes | 222/66 |
| 2,954,028 | 9/1960 | Smith | 128/214 |
| 2,971,366 | 2/1961 | Tomkow | 73/3 |
| 2,989,052 | 6/1961 | Broman | 128/214 |
| 3,001,397 | 9/1961 | Leonard | 73/194 |
| 3,017,885 | 1/1962 | Robicsek | 128/214 |
| 3,034,504 | 5/1962 | Winsor et al. | 128/214 |
| 3,037,384 | 6/1962 | Good | 73/211 |
| 3,049,918 | 8/1962 | Sparkuhl | 73/209 |
| 3,101,710 | 8/1963 | Koehn | 128/214 |
| 3,157,481 | 11/1964 | Bujan | 55/417 |
| 3,166,107 | 1/1965 | Swenson et al. | 141/145 |
| 3,198,009 | 8/1965 | Fishman et al. | 73/211 |
| 3,207,372 | 9/1965 | Evans | 222/67 |
| 3,216,418 | 11/1965 | Scislowicz | 128/214 C |
| 3,227,173 | 1/1966 | Bernstein | 137/192 |
| 3,241,365 | 3/1966 | Schroeder et al. | 73/211 |
| 3,277,708 | 10/1966 | Reynolds et al. | 73/211 |
| 3,298,367 | 1/1967 | Bergman | 128/214 R |
| 3,299,904 | 1/1967 | Burke | 137/315 |
| 3,316,935 | 5/1967 | Kaiser et al. | 137/595 |
| 3,321,970 | 5/1967 | Walker, Sr. et al. | 73/211 |
| 3,340,871 | 9/1967 | Jellies | 128/214 |
| 3,450,164 | 6/1969 | Walker, Jr. | 138/44 |
| 3,460,526 | 8/1969 | McKirdy et al. | 128/2.05 |
| 3,487,808 | 1/1970 | Perkins | 116/117 |
| 3,498,316 | 3/1970 | Pinder et al. | 137/595 |
| 3,550,619 | 12/1970 | Halasz et al. | 137/595 |
| 3,604,420 | 9/1971 | Vallancourt | 128/275 |
| 3,605,496 | 9/1971 | Wenham | 73/202 |
| 3,626,938 | 12/1971 | Versaci | 128/214 B |
| 3,667,464 | 6/1972 | Alligood, Jr. | 128/214 C |
| 3,677,248 | 7/1972 | McPhee | 128/227 |
| 3,690,318 | 9/1972 | Gorsuch | 128/214 E |
| 3,756,233 | 9/1973 | Goldowsky | 128/214 C |
| 3,759,098 | 9/1973 | Logsdon et al. | 73/205 R |
| 3,785,378 | 1/1974 | Stewart | 128/214 C |
| 3,796,245 | 3/1974 | Wildensteiner | 150/1 |
| 3,803,914 | 4/1974 | Noiles | 73/209 |
| 3,805,612 | 4/1974 | Shiba | 73/211 |
| 3,807,397 | 4/1974 | Noiles | 128/214 C |
| 3,826,137 | 7/1974 | Clarke | 73/194 R |
| 3,838,599 | 10/1974 | Purtell | 73/211 |
| 3,851,526 | 12/1974 | Drexel | 73/202 |
| 3,851,668 | 12/1974 | Benjamin | 137/625.3 |
| 3,931,818 | 1/1976 | Goldowsky | 128/214 C |
| 3,938,539 | 2/1976 | Strouth et al. | 137/202 |
| 3,941,126 | 3/1976 | Dietrich et al. | 128/214 R |
| 3,949,745 | 4/1976 | Howell | 128/214 C |
| 3,963,024 | 6/1976 | Goldowsky | 128/214 C X |
| 3,967,620 | 7/1976 | Noiles | 128/214 C |
| 3,998,097 | 12/1976 | Akashi et al. | 73/211 |
| 4,043,332 | 8/1977 | Metcalf | 128/214 E |
| 4,056,100 | 11/1977 | Noiles | 128/214 C |
| 4,079,737 | 3/1978 | Miller | 128/214 R |
| 4,099,527 | 7/1978 | Howell | 128/214 C |
| 4,136,692 | 1/1979 | Goldowsky | 128/214 C |
| 4,136,693 | 1/1979 | Dyke | 128/214 C |
| 4,223,695 | 9/1980 | Muetterties | 128/214 G |
| 4,256,103 | 3/1981 | Mylrea | 128/214 R |

FOREIGN PATENT DOCUMENTS

| | | | |
|---|---|---|---|
| 817387 | 7/1959 | United Kingdom | 128/214 C |
| 1182016 | 2/1970 | United Kingdom | 128/214 C |

Primary Examiner—Dalton L. Truluck
Attorney, Agent, or Firm—Kane, Dalsimer, Kane, Sullivan & Kurucz

[57] ABSTRACT

A medical fluid flow rate controller and method for its use are disclosed. The controller is particularly suited for intravenous liquid administration and comprises three chambers in series between the intravenous liquid source and the patient. The first and second chambers are movable vertically with respect to each other and are gas phase pressure-equalized. Accordingly, the pressure differential available for flow from the first to the second chamber through the flow restrictor employed is known. Thus, the device may be precalibrated and marked with flow rates corresponding to different relative heights of the first chamber. Liquid entering the second chamber is pulled through a hydrophilic membrane into the third because the third operates at a lower pressure than the second. That configuration prevents the patient's movements from affecting the pre-set flow rate between the first and second chambers.

14 Claims, 13 Drawing Figures

MEDICAL FLUID FLOW RATE CONTROLLING DEVICE

BACKGROUND OF THE INVENTION

Numerous devices have been suggested for use in administering medical fluids to patients. In particular, there have been numerous attempts to design a reliable, accurate intravenous flow rate controller that is inexpensive enough to be disposable.

Desirably, such a device should handle a wide range of flow rates, be able to be quickly and accurately set to the desired flow rate, maintain the initially set rate, be easy to prime, handle a wide range of flows, reset automatically to the desired primary flow rate after any secondary fluid delivery ends, and stop fluid delivery before air enters the tube leading from the device to the patient.

If a device can do those things, chances for a medical emergency caused by excessive or insufficient flow of medication or by an air embolism from the procedure are reduced. Additionally, demands on nursing time are lessened because frequent readjustment to the initially set flow rate is not needed and hospital costs are lowered since a hospital need keep only one type of device in stock to handle both pediatric and adult patients (the typical flow rates are significantly different).

The classic intravenous metering set comprises a fluid supply container (commonly of 1 liter volume), a drip chamber, tubing from the bottom of the drip chamber to a needle in the patient, and a device to pinch the tubing to control the flow. Fluid from the supply container drips into the chamber through a standard size cannula at a rate determined by the internal cannula fluid pressure at the exit and the gas phase (head) pressure in the chamber (controlled indirectly by pinching the tubing).

The cannula is supposed to deliver a fixed number of drops per milliliter (typically 15, 20, or 60), and flow rate is set by pinching the tube to achieve a number of drops per unit time equivalent to the prescribed number of milliliters of medication per hour. However, coldflow of the tubing material where pinched, which enlarges the cross-sectional flow path, and, in some systems, lowering of the fluid level in the supply container as fluid administration progresses may cause the flow rate to vary significantly from that initially set. Additionally, the flow rate usually will change with variations in the patient's venous pressure and vertical movement of the needle's point of entry.

Numerous attempts have been made to provide metering devices that are free from these problems. For example, U.S. Pat. No. 3,851,668 discloses a metering device having a flexible cylindrical housing and a ball movable therein. The housing has a plurality of vertical grooves of different lengths, widths, and depths on its inside wall. Fluid enters the housing above the ball and flows down through one or more of the grooves. The ball is moved vertically to change the total groove cross-sectional area available for flow.

U.S. Pat. Nos. 3,756,233 and 3,931,818 disclose two-chamber intravenous metering devices in which the fluid flow rate is controlled by varying the relative height of the chambers. The device of U.S. Pat. No. 3,931,818 makes use of tubing having a standard pressure drop to fluidly connect the two chambers and the chambers are gas phase pressure-equalized.

U.S. Pat. Nos. 3,207,372, 3,227,173, and 3,963,024 disclose devices having float check valves to prevent air from entering the tubing leading from the device to the patient when the liquid in each device is exhausted. U.S. Pat. Nos. 3,967,620 and 4,056,100 disclose the use of hydrophilic material acting as membrane valves for the same purpose. Additionally, the devices of U.S. Pat. No. 3,963,024 utilize two fluid chambers that are gas phase pressure-equalized.

However, none of these patents provides a reliable, accurate, low-cost intravenous fluid flow rate controller that can maintain the initially set flow rate, is easy to prime, resets to the primary flow rate after any secondary fluid administration ends, and controls flow rate over a wide range of flows.

SUMMARY OF THE INVENTION

An invention providing a device meeting these requirements has now been discovered. Broadly, the apparatus of this invention comprises:

(a) a first chamber having a liquid inlet, a liquid outlet, and a gas phase connection, said liquid inlet designed to receive liquid from the supply of medical fluid;

(b) a second chamber having a liquid inlet, a liquid outlet, and a gas phase connection, said first chamber movable vertically with respect to the second chamber;

(c) gas phase pressure equalization means for equalizing the gas phase pressures in those chambers;

(d) first liquid connecting means fluidly connecting the liquid outlet of the first chamber to the liquid inlet of the second chamber, said first liquid connecting means having at least one flow restrictor in the fluid flow path through which a known quantity of liquid flows when a given differential pressure exists across it;

(e) a third chamber having a liquid outlet from which liquid passes to the patient and a liquid inlet for receiving liquid from the second chamber; and (f) second liquid connecting means fluidly connecting the liquid outlet of the second chamber to the liquid inlet of the third chamber, said second liquid connecting means having a membrane valve in the flow path which when wet passes liquid but not gas under normal operating conditions.

In other embodiments, the one or more flow restrictors are cannulae, the second and third chambers are in the same housing, the flow restrictor provides the only significant pressure drop in the fluid flow path from the first chamber to the second chamber, indicia on the device correspond to different vertical heights of the first chamber and different flow rates of liquid through the flow restrictor, and the device contains means to control the flow of secondary fluid, halt temporarily the flow of primary fluid, and restart the primary flow at its previously set rate after secondary flow ends.

Another aspect of the invention relates to methods of controlling the flow of medical fluids to patients utilizing various embodiments of the device.

BRIEF DESCRIPTION OF THE DRAWINGS

To facilitate further description of the invention, the following drawings are provided in which:

FIG. 10 is an exploded view of the device, with a detail view (FIG. 10A) showing how the membrane filter is held in place;

It should be understood that these drawings are provided for illustrative purposes only and should not be construed to limit the scope of the invention. It should also be understood that for the sake of clarity details shown in one view may not be shown in other views. For example, details of most of the flexible tubing inside the device of FIGS. 2-12 are omitted from one or more of those drawings.

DETAILED DESCRIPTION OF THE INVENTION

Figures 1, 2:
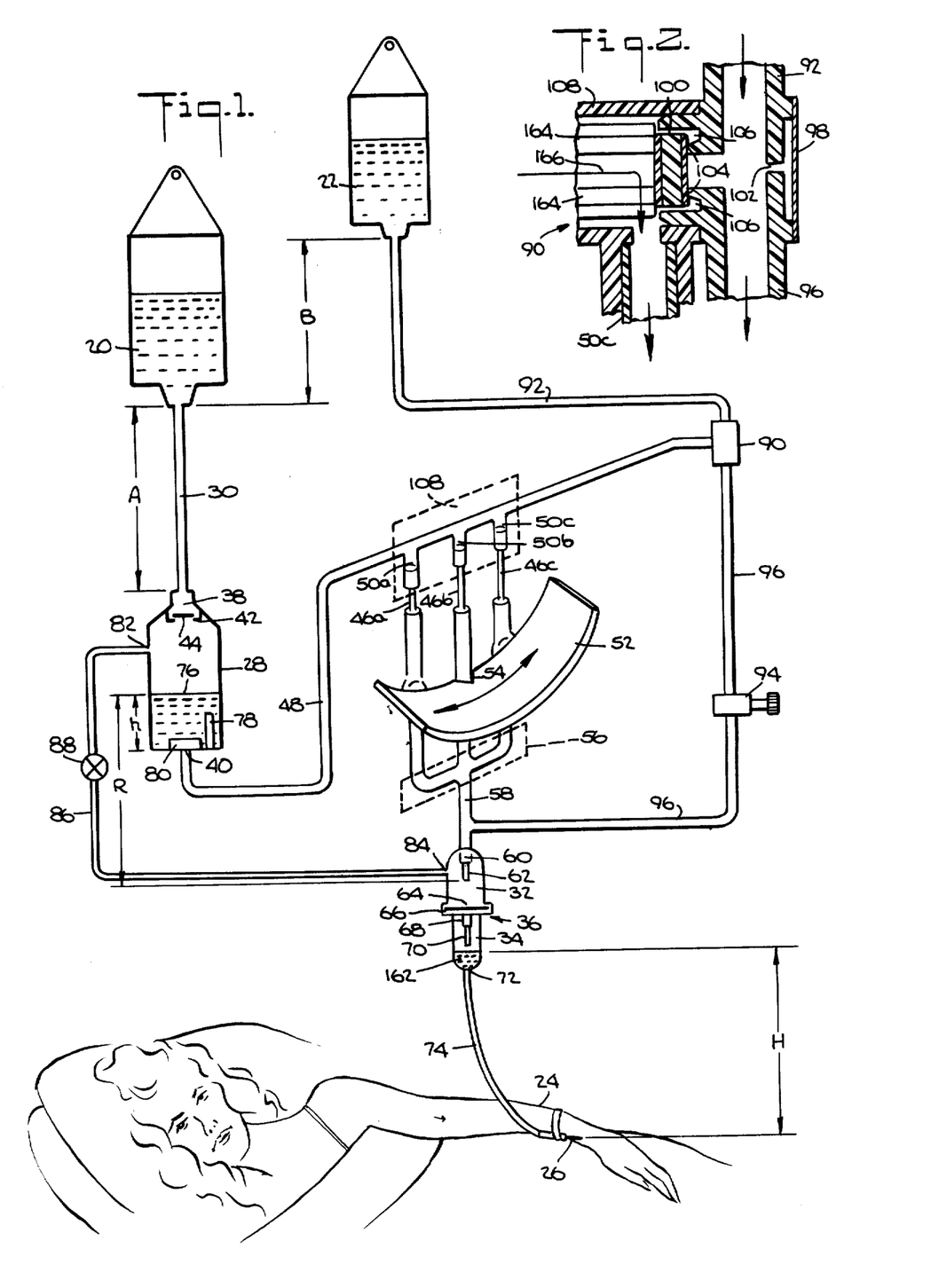
FIG. 1 is a schematic of the fluid flow scheme in a preferred device according to the present invention used to administer medical liquid intravenously to a patient.
FIG. 2 is an enlarged detail view of a valve assembly used in a preferred device utilizing the flow scheme of FIG. 1, said valve assembly used when liquid from a secondary liquid source is to be administered to a patient.

FIG. 1 is a schematic of a preferred device embodying the present invention. The flow rates of primary intravenous fluid from supply 20 and secondary intravenous fluid from supply 22 to needle 26 in patient's arm 24 are controlled by the new device. Broadly, primary fluid flows from supply 20 into first chamber 28, into one of three cannulae 46, out of dropping needle 62 in second chamber 62, through membrane valve 66, into third chamber 34, and then to the patient. The secondary fluid flows from supply 22 into valve 90 in which the flow is split into two parallel but unequal streams, which are through the cannula 46 that was being used for the primary fluid and through line 96. The two parallel flows rejoin and then, as for the primary fluid, pass through dropping needle 62, membrane valve 66, third chamber 34, and into the patient. Administration of secondary fluid temporarily halts the flow of primary fluid; when the secondary supply is exhausted primary flow restarts at its originally set flow rate.

More specifically, primary fluid leaves supply 20 through tubing 30 and enters first chamber 28 through inlet 38 containing check valve 42. Movable valve member 44 can move up and down, down to admit primary liquid and up to block the flow of fluid from first chamber 28 back into tubing 30. Liquid 76 leaves first chamber 28 through hydrophilic filter 80 at outlet 40, passes through tubing 48 and into header 108 having three branches 50. Each branch 50 has a cannula 46 of a different size, and slide valve 52 contains notch 54.

In FIG. 1, notch 54 is disposed around and does not pinch the flexible tubing for branch 50b, while branches 50a and 50c are pinched shut between the back edge of slide valve 52 and another member (not shown). Accordingly, fluid entering header 108 passes through cannula 46b but not through cannulae 46a or 46c. If slide valve 52 were moved so that notch 54 were around the tubing for branch 50a or 50c, fluid would flow, respectively, through cannula 46a and 46c only.

The three branches join at collection header 56, from which the fluid flows through tubing 58 into second chamber 32 via inlet 60 having dropping needle 62, from which the fluid falls in the form of drops onto membrane filter 66 at outlet 64. Liquid passes through membrane filter 66 into third chamber 34 via inlet 68 leading to dropping needle 70. The liquid leaves third chamber 34 via outlet 72 from a small pool of fluid 162 at the bottom of the chamber and flows through tubing 74 into needle 26 in patient's arm 24. Second chamber 32 and third chamber 34 are located in the same housing 36 and are separated by membrane valve 66.

The gas phase in first chamber 28 (above liquid 76) and the gas phase in second chamber 32 (which chamber contains essentially only gas) are pressure equalized through tubing 88, which connects outlets 82 and 84 of the two chambers. Priming valve 88 in tubing 86 is normally open.

Before the device is used for the first time, the entire device, including the three chambers and connecting tubing, contains only air. To use it, priming valve 88 is closed, slide valve 52 is moved so that all three branches can pass liquid, and primary supply 20 is fluidly connected to tubing 30 so that liquid flows from supply 20 through tubing 30, through inlet 38 and valve 42, and to the bottom of first chamber 28.

As air leaves the first chamber through hydrophobic membrane valve 78, the liquid rises past the top of hydrophilic membrane valve 80 and flows through outlet 40 into tubing 48 (hydrophobic valve 78 is higher than hydrophilic valve 80). The liquid then flows into header 108 and through all three branches 50 until the three cannulae 46 are reached. Liquid temporarily stops flowing out of first chamber 28 because the cannulae provide the only significant flow restriction (or pressure drop) from outlet 40 to inlet 60. That is, additional pressure is required to force the liquid through the cannulae. Thus, since the liquid flowing into first chamber 28 from supply 20 cannot leave, the level of liquid 76 starts to rise and the liquid forces additional air out of the first chamber 28 through hydrophobic membrane valve 78. The gas phase pressure has to this point remained essentially at atmospheric.

When the liquid rises sufficiently to cover membrane 78, air can no longer leave and first chamber 28 starts to pressurize. Pressurization caused by fluid entering from supply 20 continues until the pressure of the gas compressed within first chamber 28 reaches the hydrostatic pressure on the fluid entering (at inlet 38).

Sometime during or at the end of pressurization, the pressure required to force the liquid through cannulae 46 is reached and liquid flow through them commences. The liquid from them passes into header 56, tubing 58, and dropping needle 62, thereby purging air through dry hydrophilic membrane valve 66 and out needle 26 (which, of course, has not yet been placed in the patient). When liquid finally wets membrane valve 66 sufficiently, air no longer can pass through it and the air in second chamber 32 becomes trapped therein (valve 88 is still closed and membrane valve 66 will not pass air). The liquid passes through membrane valve 66 into inlet 68 in third chamber 34, through dropping needle 70, through outlet 72 into tubing 74, and out needle 26.

Reference numeral 162 denotes the liquid hold-up at the bottom of the third chamber 34.

Fluid continues to flow at a high rate into first chamber 28 and out needle 26 until slide valve 52 is moved out of the priming position and notch 54 engages the tubing for one of the three branches 50. Then, as described above, liquid flows through only one of the three cannulae 46. Additionally, at the end of the priming procedure valve 88 is opened, allowing the gas pressure in first and second chambers 28 and 32 to equalize.

The height of liquid in supply 20 typically varies from approximately 16 inches (406 mm) for a full 1-liter IV bag down to 0 inches when empty. Tubing 30 is approximately 6 inches (152 mm) long (dimension A). Thus, the hydrostatic head on fluid entering at inlet 38 is typically between approximately 6 and 22 inches (152 and 559 mm, respectively). For the device of FIGS. 2 to 12, this difference in head causes the level of fluid 76 above membrane 78 to vary from 0.125 to 0.185 inches (3.2 to 4.7 mm). Also, for the same device, dimension h (the height of fluid above outlet 40) is approximately 0.375 inches (9.5 mm) and because first chamber 28 is movable vertically with respect to second chamber 32, vertical dimension R (the top of fluid 76 to the end of dropping needle 62) varies from approximately 1.75 to 4.5 inches (45 to 114 mm).

First and second chambers 28 and 32 are gas phase pressure-equalized by tubing 86, thus, a pressure loss equal to hydrostatic head R (1.75 to 4.5 inches—45 to 114 mm—of liquid) is what is available to move the liquid from first chamber 28 to the end of dropping needle 62. The device is designed so that essentially all of the pressure loss occurs in whichever cannula is selected, that is, the cannula provides the only significant pressure drop in the fluid path from outlet 40 to the end of dropping needle 62. Accordingly, for each cannula, a specific value of R causes a specific predeterminable flow rate of liquid and, therefore, the device can be premarked with indicia at different relative first chamber heights corresponding to those flow rates.

Those premarked flow rates will be correct within the accuracy required for liquids not varying significantly in specific gravity or viscosity from that of the liquid used to calibrate and premark the device (e.g., plus or minus 10% in viscosity). For example, if the device is premarked with flow rates for saline solution, having a viscosity at room temperature of about 1 cp, the device may be used with fluids having viscosities up to 1.1 cp without significant error. Of course, the device may be calibrated and premarked for higher viscosity fluids.

The gas phase pressure in third chamber 34 is below atmospheric. It is equal to atmospheric pressure minus the pressure equal to the height of fluid from the top of fluid 162 to the discharge end of needle 26 (dimension H) plus the venous pressure. That typically is equal to a vacuum of approximately 30 inches (762 mm) of liquid (H is approximately 36 inches—914 mm—and venous pressure is typically 5 to 6 inches—127 to 152 mm).

The gas phase pressure in second chamber 32 is above atmospheric and is the same as the gas phase pressure in first chamber 28 or between 6 inches and 22 inches (152 and 559 mm) of liquid gauge. Thus, the pressure differential drawing liquid that falls from dropping needle 62 onto membrane 66 into third chamber 34 is from 36 (6 plus 30) to 52 (22 plus 30) inches (914 to 1321 mm) of liquid. Accordingly, the flow rate of liquid from supply 20 through dropping needle 70 is independent of the patient's raising or lowering the needle's point of entry (assuming it is not raised sufficiently to decrease the driving force on the liquid passing through membrane 66 from second chamber 32 to zero or less).

If secondary liquid is to be administered, the discharge of secondary supply 22 is placed at a level higher than the discharge of primary supply 20 (dimension B), typically 9 inches (229 mm) higher. Tubing 92 from supply 22 is connected to valve assembly 90, and assembly 90 is connected to header 108 and to tubing 58 by tubing 96. A small amount of secondary fluid then flows along tubing 48 to header 108 and forces liquid back into first chamber 28 because of the higher hydrostatic head on liquid leaving supply 22. That raises the level of liquid in first chamber 28, which further pressurizes the gas therein. That, in turn, causes inlet valve member 44 to move up within valve 42 and temporarily halt the flow of primary fluid into first chamber 28. Since priming valve 88 is open, the gas phase pressure in second chamber 32 also rises.

Secondary fluid forced into header 108 also flows through whichever branch 50 was being used to meter the primary fluid. The major flow of secondary fluid, however, is through tubing 96. The minor flow of secondary fluid through one of the branches 50, cannula 46, header 56, and tubing 58 mixes with the major flow through tubing 96. The combined flow enters second chamber 32 through inlet 60, flows out of dropping needle 62, out outlet 64, through hydrophilic membrane valve 66, into third chamber 34 through inlet 68, through dropping needle 70, and to the patient through tubing 74 and needle 26. The flow rate of secondary fluid out of dropping needle 70 in third chamber 34 is adjusted by valve 94.

Typically, secondary fluid is administered at comparatively high flow rates and in volumes less than 100 cc. After secondary supply 22 is exhausted, the level of liquid in tubing 92 falls, thereby decreasing the gas phase pressure in first chamber 28. At some point, the liquid in tubing 92 falls to a level such that the hydrostatic pressure on primary fluid entering first chamber 28 at inlet 38 is greater than the gas phase pressure. When this happens, valve member 44 moves down and the flow of primary fluid into first chamber 28 resumes. Because neither the relative height of the first and second chambers nor slide valve 52 had to be moved to administer secondary fluid, the primary fluid resumes its flow out of first chamber 28 and into the patient at the rate set before administration of the secondary fluid commenced.

Figures 11, 12:
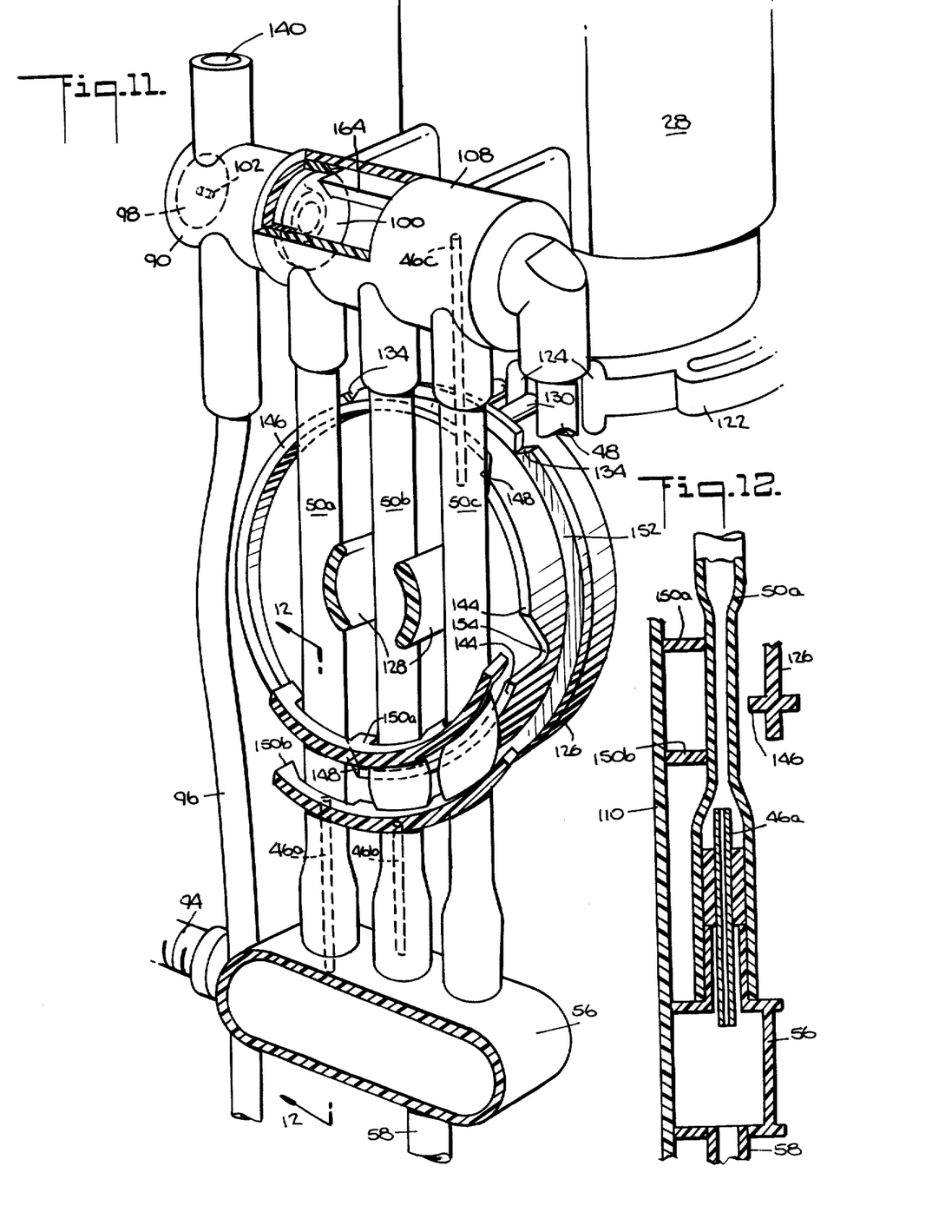
FIG. 11 is an enlarged perspective detail view of the back of the device showing the three cannulae used therein in their respective tubing.
FIG. 12 is a side sectional view taken along line 12—12 of FIG. 11.

FIG. 2 is a detailed view, showing valve assembly 90 in a device embodying the principles of FIG. 1. Valve 100 in valve assembly 90 comprises three layers: a central compressible foam rubber disc and two matching silicone rubber discs, one on either side of the foam rubber. In FIG. 2 the foam core of valve 100 is fully expanded between support ribs 164 of header 108 and valve seat 104. (Upper rib 164 is also shown in FIG. 11.) When primary fluid flows it enters heater 108 and passes next to lower rib 164 into one of three branches, as indicated by arrow 166. The right silicone rubber disc of valve 100 is seated on valve seat 104, thus preventing primary fluid from entering tubing 92 or 96. That ensures that all the primary fluid leaving primary supply 20 and entering header 108 passes through the cannula selected (in FIG. 2, branch 50c and cannula 46c).

When secondary fluid flows into valve assembly 90 via tubing 92, the major part of the flow passes directly into tubing 96 and to the patient, as explained above. All of the air in tubing 92 and 96 passes through opening 102 and out of the device through hydrophobic membrane valve 98. The higher hydrostatic head on the secondary liquid to the right of valve 100 pushes the right silicone rubber disc of valve 100 to the left, thereby temporarily compressing the central foam rubber core and allowing secondary fluid to flow through passageway 106 into header 108. As explained above, this minor flow of secondary fluid causes the flow of primary fluid into first chamber 28 to stop temporarily by closing inlet valve 42. Additionally, some of this secondary fluid passing into header 108 flows through whichever cannula was being used for the primary fluid (in this case, cannula 46c).

When the hydrostatic head on the secondary fluid to the right of valve 100 is no longer sufficient to keep valve 100 open, the flow of secondary fluid into header 108 stops, thereby removing the hydrostatic back-pressure on the liquid at the bottom of first chamber 28 caused by the secondary fluid. There is then no extra liquid phase pressure to maintain the additional compression on the gas in first chamber 28. The gas expands and its pressure falls until inlet valve 42 reopens and primary liquid flow resumes, as explained above. Tubing 96 remains filled with secondary liquid.

Figure 3:
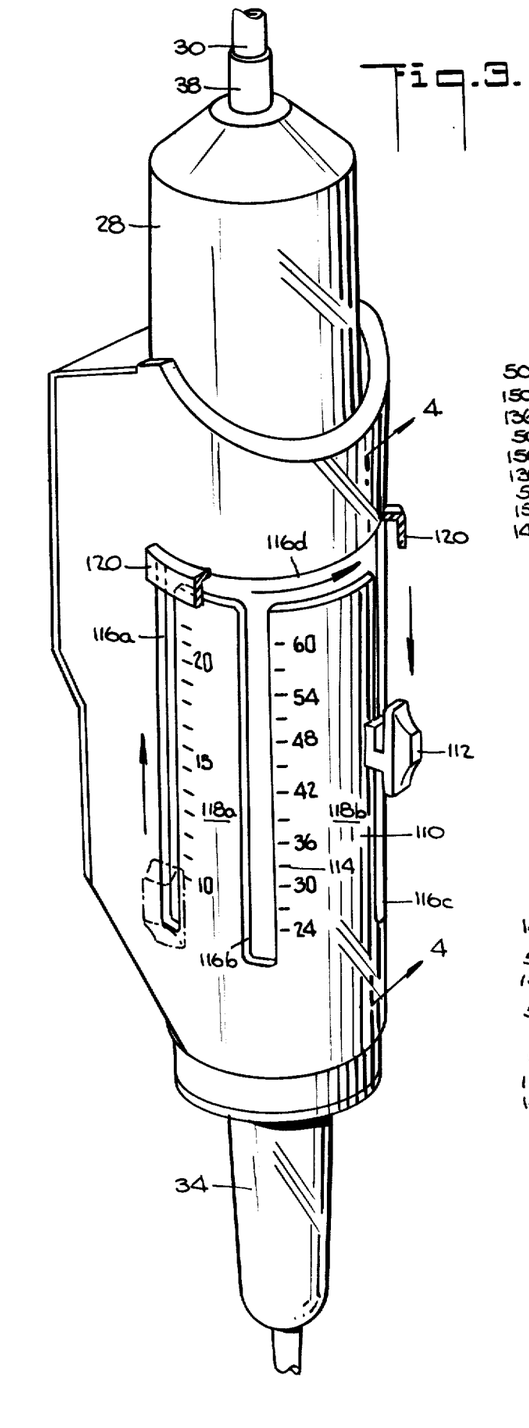
FIG. 3 is a perspective view of the same preferred device utilizing the flow scheme of FIG. 1 whose valve assembly is shown in FIG. 2.

FIG. 3 is a perspective view of the preferred device containing valve assembly 90 of FIG. 2 and constructed in accordance with the schematic of FIG. 1. First chamber 28, having tubing 30 from primary supply 20 (not shown) connected to inlet 38, is moved up and down within housing 110 by button 112, which moves within slot 116. The slot comprises three vertical portions, 116a, b, and c, and one horizontal portion, 116d. Because of the configuration of the slot, housing portions 118a and b are connected to the rest of housing 110 at only their bottom ends. Thus, shield 120 (only a portion of which is shown) is provided to prevent excessive outward movement of those portions. Shield 120 is constructed so that arm 168 of button 112 (FIG. 6) is free to slide under it when the button is in slot portion 116d.

Each slot portion 116a, b, and c corresponds to selection of one of the three cannulae, as will be described below. Button 112 in phantom line corresponds to selection of branch 50a with cannula 46a. To change, for example, to cannula 46c, which is used for the highest range of flow rates, button 112 is moved up in slot portion 116a, pushed to the right in slot portion 116d, and then pushed down into slot portion 116c to the desired level. In this device, dropping needle 62 in second chamber 32 is held stationary in housing 110 and first chamber 28 is movable vertically within the housing to vary dimension R (FIG. 1), thereby to set the flow rate. Indicia 114 to the sides of slot portions 116a, b, and c are in milliliters per hour and correspond to the particular cannula and height R chosen.

Figure 4:
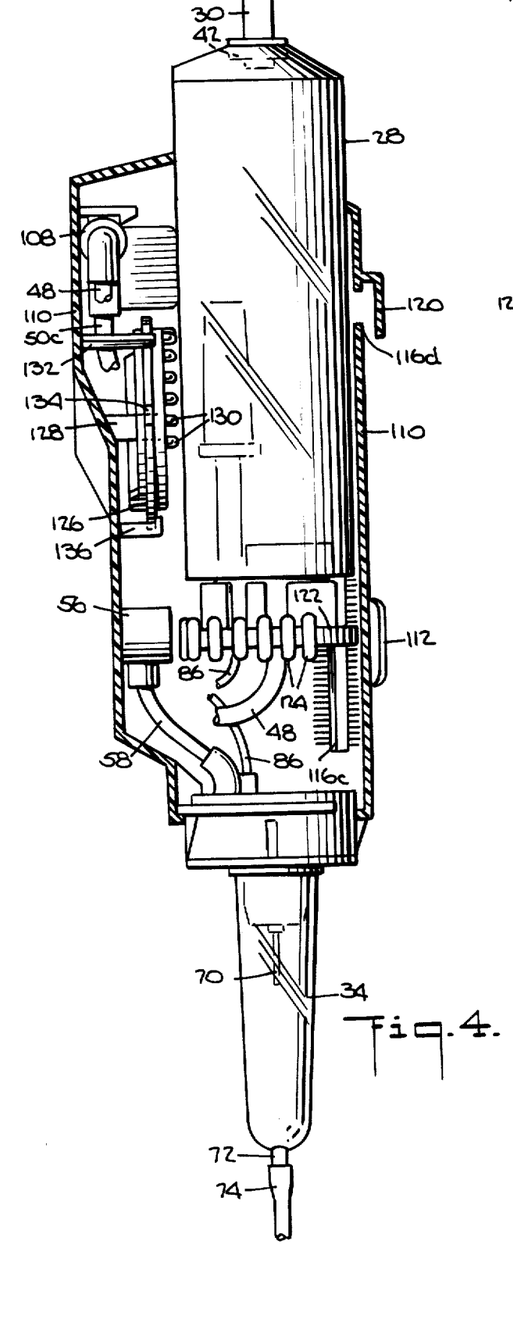
FIG. 4 is a side sectional view of the device taken along line 4—4 of FIG. 3.

FIG. 4 is a sectional view of the device taken along line 4—4 of FIG. 3. Button 112 is connected to lever gear 122 having teeth 124. The gear is rotatably connected to the bottom of first chamber 28. When button 112 is pushed up as high as it will go, first chamber 28 is pushed to its highest and teeth 124 mesh with teeth 130 on horseshoe gear 126, which is rotatably mounted on mounts 128 connected to the back wall of housing 110.

Detent 132 rides on the rim of horseshoe gear 126 (see also FIG. 10), which rim has four notches 134. Three notches are positioned to mate with detent 132 when button 112 is in one of the slot portions 116a, b, or c. The fourth notch 134 mates with detent 132 when button 112 is in horizontal slot portion 116d and is moved past the highest flow range, a position denominated "Prime" on housing 110 (see FIG. 5). Detent 132 and the notches cooperate to prevent movement of horseshoe gear 126 when first chamber 28 moves down in housing 110, which unmeshes teeth 124 (on lever gear 122) and teeth 30 (on gear 126).

Retaining clips 136, mounted on the back wall of housing 110, keep horseshoe gear 126 from slipping off of or tilting on mounts 128. Also shown in FIG. 4 are dropping needle 70 in third chamber 34 and tubing 74 connected to outlet 72.

Various fluid connecting means (or tubing) are shown cut-away for clarity. Tubing 48 carries primary liquid from the bottom of first chamber 28 to header 108, mounted on the rear wall of housing 110. Tubing 86, for gas phase pressure equalization, runs from first chamber 28 to the bottom of housing 110, where second chamber 32 (not shown) and third chamber 34 are located. The three branch lines 50 (only one of which, 50c, is shown) run from header 108 down to collection header 56 and tubing 58 runs from header 56 to the inlet of the second chamber.

Figure 5:
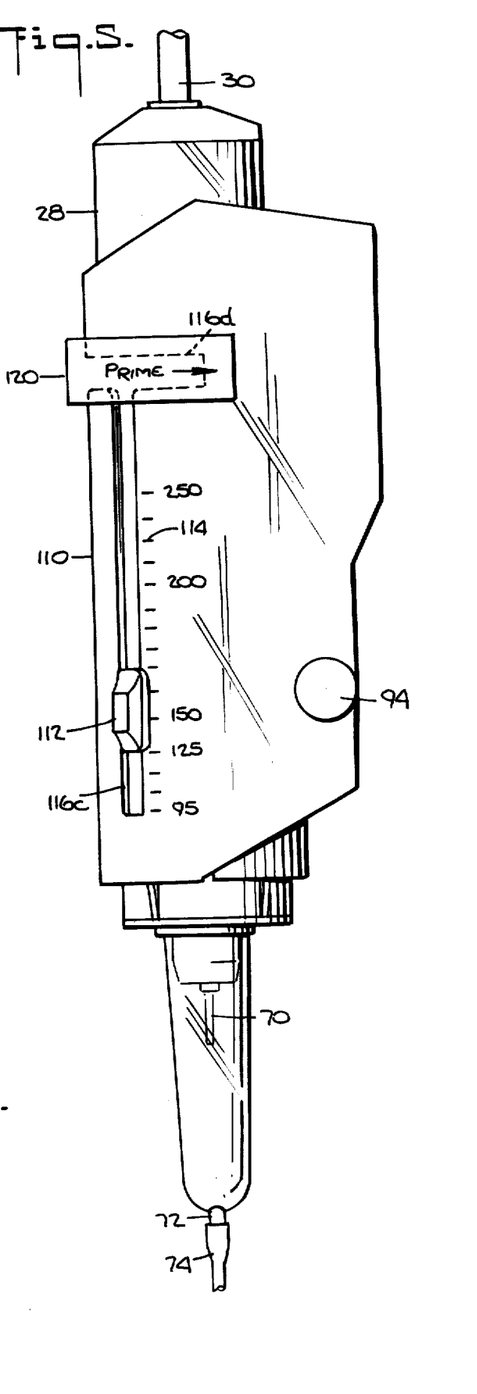
FIG. 5 is a view of the device from the side opposite that of FIG. 4.

FIG. 5 shows the outside of the device opposite the side of FIG. 4. Shield 120, which follows slot portion 116d, is shown. Button 112 is in slot portion 116c, allowing metering of primary flows in the 95 to 250 ml/h range. Valve 94 allows flow rate control of the secondary fluid.

Figure 6:
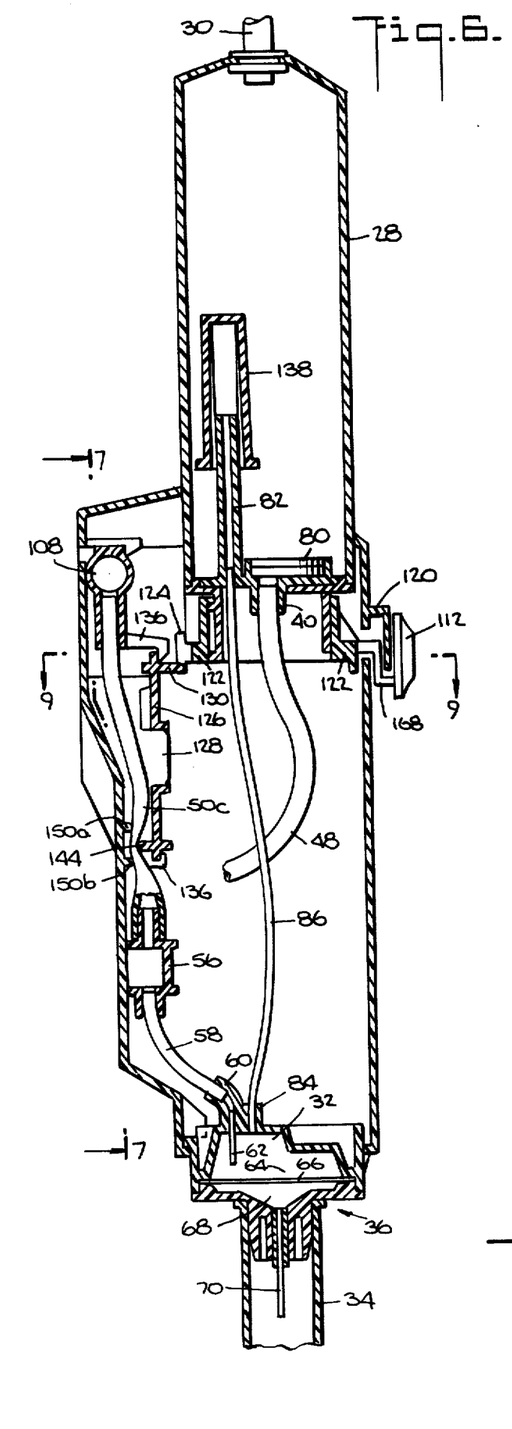
FIG. 6 is a side sectional view of the device.

FIG. 6 is a view of the same side of the device as in FIG. 4 but with the entire device in section. Chamber 28 has been raised to its highest position by button 112 and teeth 124 and 130 of gears 122 and 126 are meshed. Arm 168 connects button 112 to lever gear 122. Tubing 86, which equalizes the gas phase pressures in first and second chambers 28 and 32, runs from gas phase connection (or riser) 82 to gas phase connection 84. Although the liquid level in chamber 28 (dimension h in FIG. 1) is only approximately 0.375 inches (9.5 mm) for this device and the riser is approximately 1.4 inches (36 mm) high, cap 138 is provided to prevent liquid entering first chamber 28 via tubing 30 from going into riser 82 and tubing 86. Liquid leaving first chamber 28 passes through hydrophilic membrane valve 80 and outlet 40 before entering tubing 48 (only a portion of which is shown) to go to header 108.

Whereas in FIGS. 3, 4, and 5 the device is shown with button 112 in slot portion 116c, that is, the device is set for the highest flow range (cannula 46c is selected), in FIG. 6 button 112 is in slot portion 116b, that is, the middle flow range (cannula 46b) is selected. Accordingly, as in FIG. 1, branch tubing for the other two cannulae must be pinched so that liquid flowing from header 108 to header 56 passes through cannula 46b only.

FIG. 6 shows how this pinching is accomplished. Back rim raised portion 144 of horseshoe gear 126 pushes a section of branch tubing 50c against upper and lower compression bars 150a and b, which are mounted on the rear wall of housing 110. That pinches tubing 50c sufficiently to prevent fluid flow through it. Another portion of back rim raised portion 144 pinches tubing 50a (not shown) with the same result. Thus, only tubing 50b (not shown) remains open. Top and bottom retaining clips 136 ensure that back rim raised portion 144 sufficiently pushes tubing 50a and c against compression bars 150.

Liquid flowing from header 108 to collection header 56 leaves the latter through tubing 58, enters second chamber 32 at inlet 60, and flows through dropping needle 62. Liquid from needle 62 drops onto and flows through hydrophilic membrane valve 66 to inlet 68 of third chamber 34. Liquid falling into inlet 68 flows to the bottom of the inlet area and then through dropping needle 70 into the main plenum of third chamber 34. Second and third chambers 32 and 34 are located in T-shaped housing 36 and are separated by membrane valve 66: above membrane 66 is outlet 64 of second chamber 32 and below membrane 66 is inlet 68 of third chamber 34.

Figure 7:
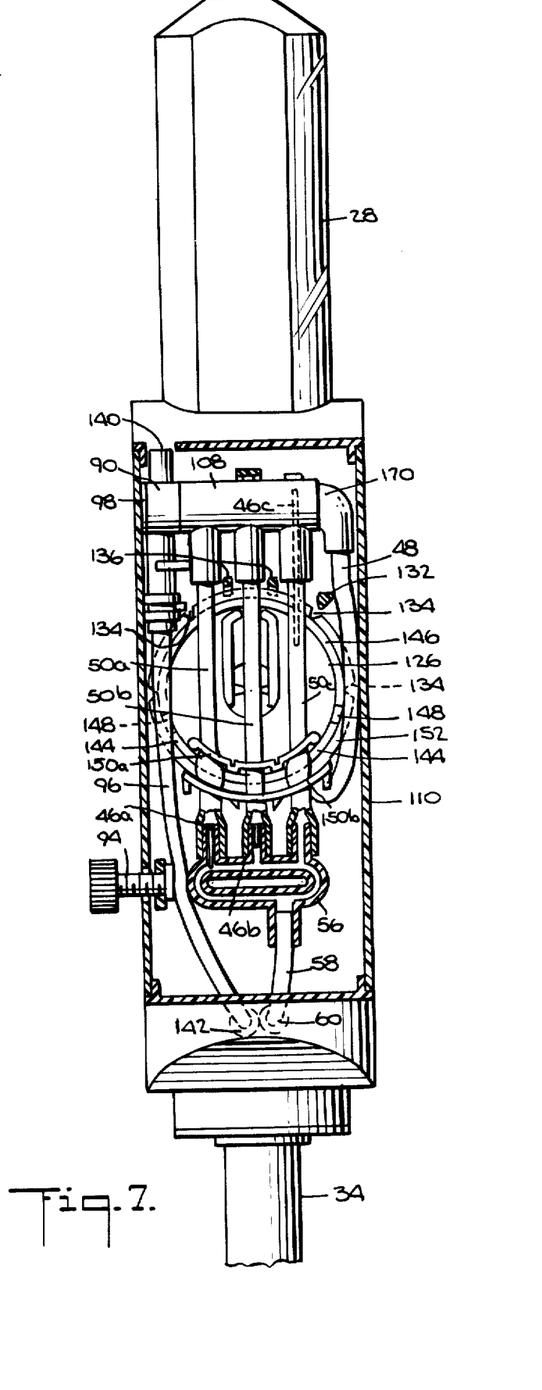
FIG. 7 is a rear view of the device taken along line 7—7 of FIG. 6.

FIG. 7 is a rear view of the device. Tubing 48 from the bottom of first chamber 28 passes up the right inside of the device to elbow 170, which leads into header 108. Branch tubing sections 50a, b, and c run from header 108 to collection header 56 and tubing 58 carries liquid from the latter to second chamber inlet 60. Each branch 50 has a cannula 46 in it. As in FIG. 6, back rim raised portion 144 is compressing branch tubing 5a and c against compression bars 150a and b to prevent flow through them. The sides of notch 154, centrally located in raised portion 144 (not shown—see FIG. 11), bracket but do not compress tubing 50b in the region between compression bars 150. That is why tubing 50b is not also compressed by raised portion 144.

Cannula 46a and b are located close to header 56; cannula 46c is located with its upper end close to the inside top of header 108 to provide a path for air in header 108 to leave when the device is primed.

The back rim of horseshoe gear 126 has raised portion 144 and lower portion 146, with two transition sloped surfaces 148. Shown in this view are the four notches 134 that mate with detent 132 and the end of the detent connected to the rear wall. Also visible are the ends of the two upper retaining clips 136, which are connected to the rear wall.

Secondary fluid supply 22 (not shown) is connected to the device by inserting a needle at the end of connecting tubing 92 (not shown—see FIG. 1) into elastomeric stopple 140. The secondary fluid then flows directly into valve assembly 90. The details of the construction and operation of valve assembly 90 are described above in connection with FIG. 2. The major portion of secondary liquid flowing through valve assembly 90 goes into tubing 96, which meets with tubing 58 at header 142 atop second chamber 32 (not shown). The minor portion of the flow goes through tubing 58, and the combined flow at header 142 goes into second chamber 32 through dropping needle 62 (not shown—see FIG. 6). Valve 94 is a screw-compression type. As valve 94 is turned clockwise to decrease the secondary fluid flow rate, tubing 96 is pinched between the end of the screw and the left end of collection header 56. Counter-clockwise rotation increases the flow rate.

Figure 8:
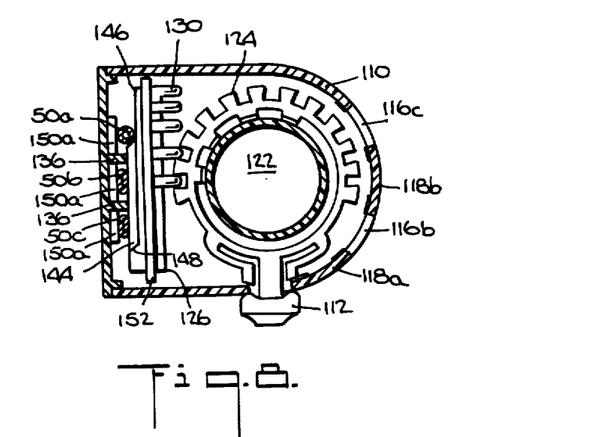
FIG. 8 is an overhead sectional view of the device similar to that of FIG. 9.
Figure 9:
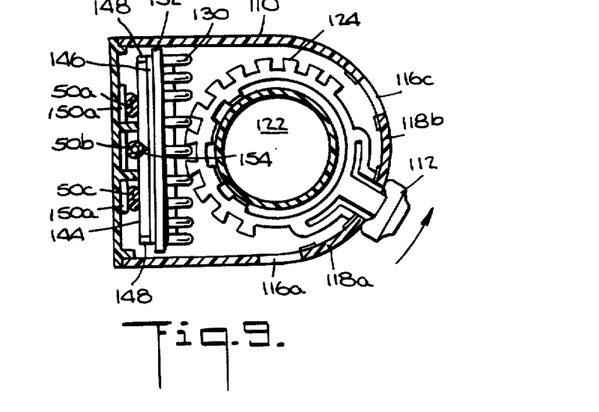
FIG. 9 is an overhead sectional view of the device taken along line 9—9 of FIG. 6.

FIGS. 8 and 9 are top sectional views taken along line 9—9 of FIG. 6. FIG. 9 shows the device in the same configuration as in FIG. 6, that is, set to the middle flow range. FIG. 8 shows the device set to the lowest flow range. In both views (FIGS. 8 and 9), teeth 124 of lever gear 122 are meshed with teeth 130 of horseshoe gear 126 and branch tubing sections 50a, b, and c are seen to be between gear 126 and upper compression bar 150a (the lower compression bar is not visible).

In FIG. 8 button 112 is set to the lowest flow range (as shown in phantom line in FIG. 3). Tubing 50b and c are both clamped shut between back rim raised portion 144 and compression bars 150. One of the inclined transition surfaces 148 (between back rim raised and lower portions 144 and 146) lies next to tubing 50a, which remains open, thereby allowing primary flow through cannula 46a only.

When button 112 is moved within slot portion 116d (FIG. 3) to the position shown in FIG. 9, gear 122 rotates counter-clockwise causing horseshoe gear 126 to rotate counter-clockwise when viewed from the front. That moves notch 154 around tubing 50b and causes the rest of back rim raised portion 144 to clamp shut branch tubing 50a and c, as in FIG. 9. Button 112 is now positioned over slot portion 116b and may be moved vertically therein.

Figures 10, 10A:
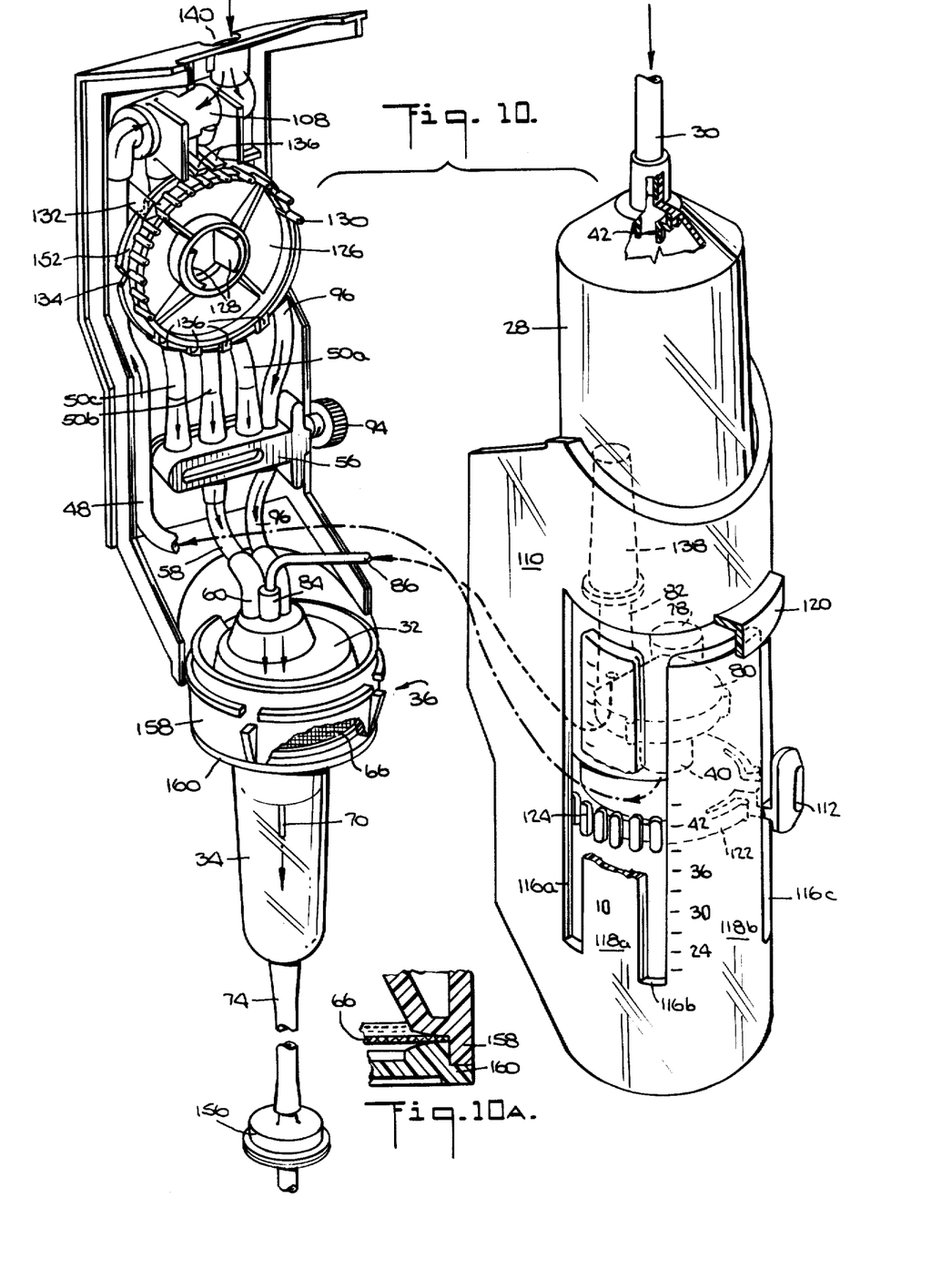

FIG. 10 is an exploded perspective view of the device showing the front of housing 110 and first chamber 28 broken away from the rear of housing 110 and second and third chambers 32 and 34. Valve 42 admits primary liquid from tubing 30 into first chamber 28. Button 112 is in slot portion 116c, that is, the device is set to the highest flow range. Shown in phantom line are hydrophobic membrane valve 78 (which allows air to leave the chamber during priming), hydrophilic membrane valve 80 (through which primary liquid from first chamber 28 passes via tubing 48 to header 108), riser 82 with cap 138 (which riser is connected to second chamber 32 by gas phase pressure equalization tubing 86), and lever gear 122.

On the rear section of housing 110, the six retaining clips 136 holding horseshoe gear 126 on mounts 128 are visible, two clips at the top of the gear and four clips at the bottom. Detent 132 and one of the four grooves in rim 152 on gear 126 are cooperating to prevent accidental rotation of gear 126. Tubing 58 (from collection header 56), tubing 86 (from riser 82), and tubing 96 (for carrying secondary fluid admitted through stopple 140) meet at the top of the smaller, raised portion of second chamber 32.

Hydrophilic membrane valve 66 separates second and third chambers 32 and 34. Liquid from the latter flows to the patient through tubing 74, which has check valve 156 in the flow path. FIG. 10A shows that membrane 66 is mounted between sidewall 158 and horizontal portion 160 of housing 36.

FIG. 11 is a rear perspective view of horseshoe gear 126, the headers, and associated tubing. In this view the device is set to the lowest flow range: gear 126 has been rotated clockwise (when viewed from the front) as far as possible. Thus, one part of back rim raised portion 144 is compressing tubing 50b and c against compression bars 150a and b, thereby preventing flow through middle and high range cannulae 46b and c, but back rim lower portion 146 is not pinching tubing 50a, thereby allowing flow through low flow range cannula 46a.

First chamber 28 is at its highest and teeth 124 and 130 of lever gear 122 and horseshoe gear 126 are meshed. Valve 100 lies between ribs 164 and valve assembly 90 and air exit port 102 and hydrophobic membrane valve 98 are visible (see FIG. 2). Secondary tubing 96 is positioned between the left end of collection header 56 and the end of the screw of valve 94.

FIG. 12 is a sectional view taken along line 12—12 of FIG. 11 and shows that with the horseshoe gear in the position shown in FIG. 11, back rim lower portion 146 does not force branch tubing 50a against compression bars 150a and b. Therefore, tubing 50a remains open and all the liquid flowing from header 108 to collection header 56 must pass through cannula 46a.

The procedure for priming and using the device of FIGS. 1-12 follows the scheme set forth above in discussing FIG. 1. With the device of FIGS. 2-12, button 112 is moved up to slot portion 116d (FIG. 3) and the button is moved to the "Prime" position (FIG. 5). That causes horseshoe gear 126 to rotate counterclockwise (when viewed from the front) as far as possible so that the raised portion 144 of the rear rim does not contact any of the three branches 50. Thus, liquid flows through all three. Also, when button 112 is moved to "Prime," a tab at the bottom of and on lever gear 122 is brought around to bend over and thereby crimp and close off pressure equalization tubing 86 near where the tubing exits from first chamber 28 (see FIG. 6, although the tab is not shown). Thus, that tab performs the function of valve 88 in FIG. 1.

Dimensions for the device of FIGS. 2-12 that have been found to be satisfactory are as follows (all values are approximate). First chamber 28 is 1.5 inches (38 mm) in diameter by 4.3 inches (109 mm) long (straight-side). Housing 110 from its top to the bottom of third chamber 34 (FIG. 4) is 8.6 inches (216 mm) long and 2.5 inches (64 mm) at its widest (not including shield 120). The other dimensions may be determined by consulting FIGS. 4-9 since they are essentially to scale. Cannula 46a, for the lowest range (10-20 ml/h), is a standard hypodermic cannula of 25 gauge size, 0.75 inches (19 mm) long; cannula 46b (20-65 ml/h), 23 gauge, 0.5 inches (13 mm) long; and cannula 46c (90-250 ml/h), 20 gauge, 1.25 inches (32 mm) long.

The hydrophilic and hydrophobic membranes used herein (reference numerals 66, 78, 80, and 98) should have sufficiently high break-through pressures and strengths and other satisfactory physical properties so that they can perform in the manner described above. Thus, hydrophilic membrane valve 66 should have a bubble point pressure of at least 5 psi (35 kPa). The pore size of membrane 66 may vary over a wide range, e.g., from about 0.1 to over 250 microns, smaller sizes providing the additional benefit of particulate filtering. The pore size of membrane 80 must be large enough so that the pressure drop through it is small compared to that through whichever cannula 46 is being used. Desirably membrane 66 is strong enough so that it can be compression fitted between members 158 and 160 (FIG. 10A) to achieve the desired result without the need for any gaskets. That simplifies fabrication. Other means for retaining the membrane in place may be used, e.g., ultrasonic bonding, which is most preferred.

The device may be made of any pharmacologically acceptable material. For the rigid members (housing 110, first chamber 28, etc.), styrene has been found to be suitable. The tubing may be of polyvinyl chloride. Whatever the material, the tubing must be resilient enough to recover from any deformation (e.g., when tubing 86 is crimped by the tab on gear 122 during priming). Cannulae 46a, b, and c and dropping needles 62 and 70 may be of Inconel or type 304 stainless steel. The membranes may be of any suitable materials. Acrylic with a pluronic acid wetting agent has been found to be satisfactory for membrane 66.

Variations and modifications will be obvious to those skilled in the art and the claims are intended to cover all modifications and variations that fall within the true spirit and scope of the invention. For example, one, two, or more than three cannulae may be used. Their sizes and the flow ranges may be changed from those described herein. Other means may be used to ensure that the primary liquid flows only through the cannula chosen. Valve 100 and header 108 may be arranged so that when secondary liquid flow commences, valve 100 halts the flow of primary liquid from header 108 to the cannula then in use. A particulate liquid outlet filter may be added to the bottom of first chamber 28. Such a filter would need a bubble point of at least 4.5 inches (114 mm) and preferably 9-10 inches (229-254 mm) and a low pressure drop compared to that of high flow range cannula 46c. Any means known in the art which ensures a constant liquid head at the inlet of the cannula may be used. For example, first chamber 28 could employ an inlet float check valve to maintain the height of liquid therein within narrow limits.

I claim:

1. An apparatus for controlling the flow rate of an intravenously administered medical liquid to a patient from a supply of medical liquid, said apparatus comprising:
   (a) a first chamber means for containing a portion of said liquid and a gas, having a liquid inlet, a liquid outlet, and a gas phase connection, said liquid inlet designed to receive liquid from the supply of medical fluid;
   (b) a second chamber means for containing a portion of said liquid and a gas, having a liquid inlet, a liquid outlet, and a gas phase connection, said first chamber means having means for moving said first chamber means vertically with respect to the second chamber;
   (c) gas phase pressure equalization means connected to the gas phase connections for equalizing the gas phase pressures in said first and second chambers;
   (d) first liquid connecting means fluidly connecting the liquid outlet of the first chamber to the liquid inlet of the second chamber, said first liquid connecting means having at least one flow restrictor in the fluid flow path through which a known quantity of liquid flows when a given differential pressure exists across it;
   (e) a third chamber means having a liquid outlet from which liquid passes to the patient and a liquid inlet for receiving liquid from the second chamber; and
   (f) second liquid connecting means fluidly connecting the liquid outlet of the second chamber to the liquid inlet of the third chamber, said second liquid connecting means having a membrane valve in the flow path which when wet passes liquid but not gas under normal operating conditions.

2. The apparatus of claim 1 wherein a cannula is used as a flow restrictor.

3. The apparatus of claim 1 wherein the second and third chambers are in the same housing and the fluid inlet to the second chamber is fluidly connected to a dropping needle positioned above the membrane filter.

4. The apparatus of claim 1 wherein the flow restrictor provides the only significant pressure drop in the liquid flow path comprising the liquid outlet of the first chamber, the first liquid connecting means, and the liquid inlet to the second chamber.

5. The apparatus of claim 1 wherein indicia on the device for different vertical heights of the first chamber correspond to precalibrated liquid flow rates through the flow restrictor.

6. An apparatus for controlling the flow rate of an intravenously administered medical liquid to a patient, from a supply of medical liquid, said apparatus comprising:
   (a) a first chamber means for containing a portion of said liquid and a gas, having a liquid inlet, a liquid outlet, and a gas phase connection, into the gas containing part of the first chamber means said liquid inlet designed to receive liquid from the supply of medical fluid;
   (b) a second chamber for containing a portion of said liquid and a gas, having a liquid inlet, a liquid outlet, and a gas phase connection, into the gas containing part of the second chamber, said first chamber means having means for moving said first chamber means vertically with respect to the second chamber;
   (c) gas phase pressure equalization means for fluidly connecting the gas phase connections of the first and second chambers so as to equalize the gas phase pressures in the first and second chambers;
   (d) first liquid connecting means fluidly connecting the liquid contact of the first chamber to the liquid inlet of the second chamber, said first liquid connecting means having at least one cannula in the fluid flow path through which a known quantity of liquid flows when a given differential pressure exists across it;
   (e) a third chamber having a liquid outlet from which liquid passes to the patient and a liquid inlet for receiving liquid from the second chamber means; and
   (f) second liquid connecting means fluidly connecting the liquid outlet of the second chamber to the liquid inlet of the third chamber, said second liquid connecting means having a membrane valve in the flow path which when wet passes liquid but not gas under normal operating conditions.

7. The apparatus of claim 6 wherein the second and third chambers are in the same housing and the fluid inlet to the second chamber is fluidly connected to a dropping needle positioned above the membrane valve.

8. The apparatus of claim 6 wherein the cannula provides the only significant pressure drop in the liquid flow path comprising the liquid outlet of the first chamber, the first liquid connecting means, and the liquid inlet to the second chamber.

9. The apparatus of claim 6 wherein indicia on the device for different vertical heights of the first chamber correspond to precalibrated liquid flow rates through the cannula.

10. An apparatus for controlling the flow rate of an intravenously administered medical liquid to a patient from a supply of medical liquid, said apparatus comprising:
   (a) a first chamber means for containing a portion of said liquid and a gas, having a liquid inlet, a liquid outlet, and a gas phase connection, said liquid inlet designed to receive liquid from the supply of medical fluid;
   (b) a housing having a second chamber means for containing a portion of said liquid and a gas, with a liquid inlet, a liquid outlet, and a gas phase connection, said first chamber means having means for moving said first chamber means vertically with respect to the second chamber;
   (c) gas phase pressure equalization means for fluidly connecting the gas phase connections of the first and second chambers so as to equalize the gas phase pressures in those chambers;
   (d) first liquid connecting means fluidly connecting the liquid outlet of the first chamber to the liquid inlet of the second chamber, said first liquid connecting means having at least one cannula in the fluid flow path through which a known quantity of fluid flows when a given differential pressure exists across it, the cannula providing the only significant pressure drop in the liquid flow path comprising the liquid outlet of the first chamber, the first liquid connecting means, and the liquid inlet to the second chamber;
   (e) a third chamber means in the housing having a liquid ouetlet from which liquid passes to the patient and a liquid inlet for receiving liquid from the second chamber; and
   (f) a membrane valve between the liquid outlet of the second chamber and the liquid inlet of the third chamber, the membrane valve capable of passing liquid when wet but not gas under normal operating conditions.

11. The device of claim 1 further comprising:
   (a) means to connect a supply of secondary liquid to the device;
   (b) means to control the flow of secondary liquid from the device to the patient;
   (c) means to automatically halt the flow of primary liquid to the patient when secondary liquid flows; and
   (d) means to automatically restart the flow of primary liquid to the patient after secondary liquid flow ends and at the same rate of primary flow existing prior to secondary liquid flow.

12. A method of controlling the flow of medical liquid to a patient comprising utilizing the apparatus of claim 1.

13. A method of controlling the flow of medical liquid to a patient comprising utilizing the apparatus of claim 6.

14. A method of controlling the flow of medical liquid to a patient comprising utilizing the apparatus of claim 10.

* * * * *